US010980632B2

(12) United States Patent
Burriesci et al.

(10) Patent No.: US 10,980,632 B2
(45) Date of Patent: Apr. 20, 2021

(54) PROSTHETIC HEART VALVE

(71) Applicant: UCL BUSINESS LTD, London (GB)

(72) Inventors: Gaetano Burriesci, London (GB);
Selim Bozkurt, London (GB);
Benyamin Rahmani, London (GB);
Michael J. Mullen, London (GB)

(73) Assignee: Fondazione RIMED, Palermo (IT)

( * ) Notice: Subject to any disclaimer, the term of this patent is extended or adjusted under 35 U.S.C. 154(b) by 454 days.

(21) Appl. No.: 15/580,641

(22) PCT Filed: Jun. 16, 2016

(86) PCT No.: PCT/GB2016/051796
§ 371 (c)(1),
(2) Date: Dec. 7, 2017

(87) PCT Pub. No.: WO2016/203241
PCT Pub. Date: Dec. 22, 2016

(65) Prior Publication Data
US 2018/0161155 A1 Jun. 14, 2018

(30) Foreign Application Priority Data
Jun. 16, 2015 (GB) ...................................... 1510547

(51) Int. Cl.
*A61F 2/24* (2006.01)
(52) U.S. Cl.
CPC .......... *A61F 2/2418* (2013.01); *A61F 2/2427* (2013.01); *A61F 2/2436* (2013.01);
(Continued)

(58) Field of Classification Search
CPC ...... A61F 2/24–2418; A61F 2230/0034; A61F 2230/001; A61F 2230/008; A61F 2250/0039; A61F 2250/0069–007
See application file for complete search history.

(56) References Cited

U.S. PATENT DOCUMENTS 7,621,948 B2 11/2009 Herrmann et al.
8,652,203 B2 2/2014 Quadri et al.
(Continued)

FOREIGN PATENT DOCUMENTS

EP 2229921 A1 9/2010
ES 2376885 T3 6/2005
(Continued)

OTHER PUBLICATIONS

International Search Report and Written Opinion, dated Oct. 4, 2016, International Application No. PCT/GB2016/051796, 15 pages.
IPO Search Report, dated Dec. 14, 2015, GB1510547.1, 3 pages.

*Primary Examiner* — Rebecca S Preston
(74) *Attorney, Agent, or Firm* — Lowe Graham Jones PLLC

(57) ABSTRACT

A prosthetic heart valve (1) for implantation at the mitral annulus of a heart, the prosthetic heart valve comprising: a support framework (10) reversibly transformable between a collapsed configuration and an expanded configuration; and one or more leaflets connected to the framework; wherein, in the expanded configuration: the support framework defines a fluid pathway through the prosthetic heart valve, the fluid pathway having a portion with a D-shaped cross section for engaging the mitral annulus; and the one or more leaflets allow fluid to pass through the fluid pathway in a first direction but prevent fluid from flowing in the opposite direction.

14 Claims, 20 Drawing Sheets

(52) U.S. Cl.
CPC ............ *A61F 2210/0014* (2013.01); *A61F 2210/0057* (2013.01); *A61F 2220/0075* (2013.01); *A61F 2230/0034* (2013.01); *A61F 2230/0095* (2013.01); *A61F 2250/0039* (2013.01); *A61F 2250/0069* (2013.01)

(56) References Cited

U.S. PATENT DOCUMENTS

| | | | |
|---|---|---|---|
| 2006/0259135 A1* | 11/2006 | Navia | A61F 2/2409 623/2.11 |
| 2007/0162112 A1 | 7/2007 | Burriesci et al. | |
| 2008/0221672 A1 | 9/2008 | Lamphere et al. | |
| 2009/0276040 A1* | 11/2009 | Rowe | A61B 17/0401 623/2.18 |
| 2011/0137397 A1 | 6/2011 | Chau et al. | |
| 2011/0224785 A1 | 9/2011 | Hacohen | |
| 2011/0264205 A1 | 10/2011 | Righini et al. | |
| 2012/0022640 A1 | 1/2012 | Gross et al. | |
| 2012/0165929 A1 | 6/2012 | Seifalian et al. | |
| 2012/0179244 A1 | 7/2012 | Schankereli et al. | |
| 2012/0239143 A1 | 9/2012 | Rankin et al. | |
| 2012/0303116 A1 | 11/2012 | Gorman, III et al. | |
| 2013/0096674 A1 | 4/2013 | Iobbi | |
| 2013/0172978 A1 | 7/2013 | Vidlund et al. | |
| 2013/0172992 A1 | 7/2013 | Gross et al. | |
| 2013/0190861 A1 | 7/2013 | Chau et al. | |
| 2013/0211508 A1 | 8/2013 | Lane et al. | |
| 2013/0296999 A1 | 11/2013 | Burriesci et al. | |
| 2013/0325112 A1 | 12/2013 | Stacchino et al. | |
| 2014/0039613 A1 | 2/2014 | Navia et al. | |
| 2014/0214157 A1 | 7/2014 | Bortlein et al. | |
| 2014/0214159 A1* | 7/2014 | Vidlund | A61F 2/2409 623/2.14 |
| 2014/0214160 A1 | 7/2014 | Naor | |
| 2014/0257476 A1 | 9/2014 | Montorfano et al. | |
| 2015/0112427 A1 | 4/2015 | Schweich, Jr. et al. | |
| 2015/0142104 A1* | 5/2015 | Braido | A61F 2/2418 623/2.18 |
| 2015/0148895 A1 | 5/2015 | Stacchino et al. | |
| 2015/0173898 A1* | 6/2015 | Drasler | A61F 2/2433 623/2.18 |

FOREIGN PATENT DOCUMENTS

| | | |
|---|---|---|
| WO | WO-2010-112844 A1 | 10/2010 |
| WO | WO-2012-052718 A1 | 4/2012 |
| WO | WO-2013-075215 A1 | 5/2013 |
| WO | WO-2014-190329 A1 | 11/2014 |
| WO | WO-2015-036790 A1 | 3/2015 |

* cited by examiner

Front view
Axometric View

Right View frame + leaflets + cuff frame + leaflets + cuff + skirt frame + leaflets + cuff + mesh

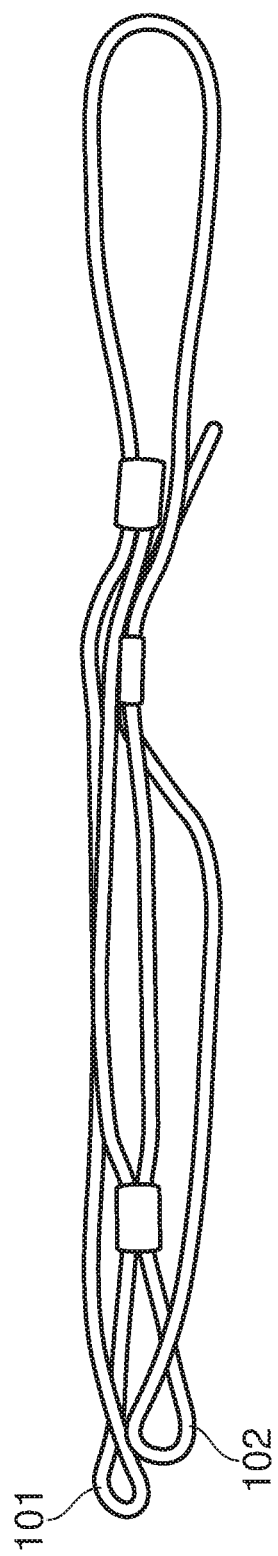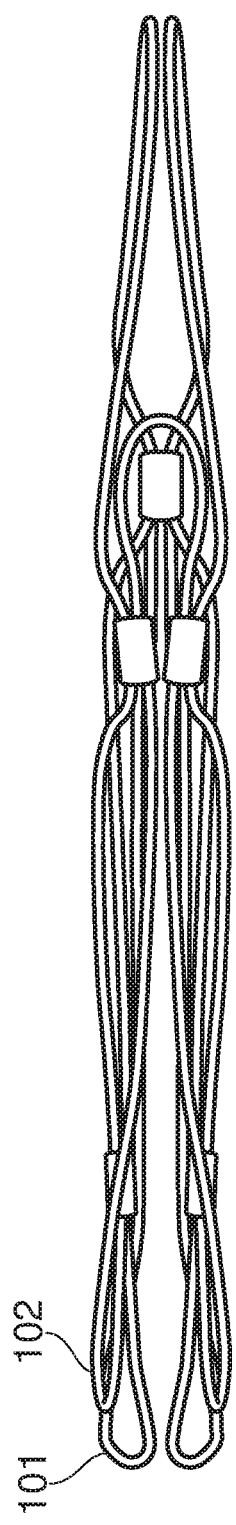
FIG. 10a
FIG. 10b

PROSTHETIC HEART VALVE

CROSS REFERENCE TO RELATED APPLICATIONS

This application is a 35 U.S.C. § 371 national phase application of PCT/GB2016/051796 (published as WO 2016/203241 A1), filed on Jun. 16, 2016, entitled "Prosthetic Heart Valve," which claims priority to Great Britain Application No. 1510547.1, filed on Jun. 16, 2015, the entire teachings of which are incorporated herein by reference in its entirety.

FIELD OF THE INVENTION

The present invention relates to a prosthetic heart valve for implantation at the mitral annulus of a heart, particularly to a prosthetic heart valve comprising a support framework that is reversibly transformable between a collapsed configuration and an expanded configuration.

BACKGROUND OF THE INVENTION

The mitral valve connects the left atrium and the left ventricle. In a healthy heart, during diastole when the left atrium fills with blood, the resulting increase in pressure will cause the mitral valve to open. This opening action provides a passageway for blood between the left atrium into the left ventricle. Atrial contraction results in the flow of blood through this passageway but at the end of the contraction the mitral valve closes, preventing blood from flowing back from the left ventricle to the left atrium.

Mitral regurgitation (MR) is one of the most common forms of heart valve disorder, occurring when blood leaks from the left ventricle into the left atrium.

This results from the failure of apposition of the mitral valve leaflets, due to degenerative or functional causes.

In recent years there has been a growing need for less invasive therapeutic approaches to valve replacement which has in turn led to the development of a number of reconstructive percutaneous treatments for MR. However; these procedures mainly contribute to alleviate the symptoms and are only suitable for very specific forms of mitral valve disease and anatomic subsets. The possibility to perform a complete percutaneous mitral valve replacement still represents an unmet need.

Transcatheter valve replacement has already been successfully applied to the treatment of pulmonary and aortic valves. However, despite the relevance of the described clinical need, the application of this approach to the mitral valve has been attempted only recently, and is still in its infancy. The overwhelming majority of prosthetic mitral valves are very closely based on aortic prosthetic valves. This invention aims to address the technical challenges associated with the geometry of the anatomical site at the mitral valve, and the more critical loading conditions specific to the mitral valve location.

Contrary to standard (open heart surgery) valves that are sutured onto the aortic annulus after dissection of the native leaflets, transcatheter valves are expanded into the diseased valve leaflets. This may result in gaps between the prosthesis and the surrounding native tissues, which would give rise to paravalvular leakage (PVL). The risk of PVL is thought to be even more prominent in the mitral position (as compared to the aortic position) due to the higher transvalvular pressure difference that exists either side of the mitral valve.

SUMMARY OF THE INVENTION

Accordingly, the present invention aims to solve the above problems by providing, according to a first aspect, a prosthetic heart valve for implantation at the mitral annulus of a heart, the prosthetic heart valve comprising: a support framework reversibly transformable between a collapsed configuration and an expanded configuration; and one or more leaflets connected to the framework; wherein, in the expanded configuration: the support framework defines a fluid pathway through the prosthetic heart valve, the fluid pathway having a portion with a D-shaped cross section for engaging the mitral annulus; and the one or more leaflets allow fluid to pass through the fluid pathway in a first direction but prevent fluid from flowing in the opposite direction.

The portion with a D-shaped cross-section should be understood to be a portion of the frame where the cross section transverse or substantially transverse to the longitudinal axis of the support framework is non-circular. The longitudinal axis of the support framework is the axis along which fluid may flow through the prosthetic valve.

The D-shaped cross section of the portion with a D-shaped cross section may also be referred to as a "bean-shaped" cross section. The D-shaped cross section exhibits a first arc which is convex and a second arc which, according to some embodiments, may be concave or straight. The second arc may also be convex, in which case it will exhibit a smaller degree of curvature as compared to the first arc.

The shape of the framework (i.e. its outer circumference) is chosen to better conform to native mitral valve. In this way, as well as reducing leakage, it is also possible to minimise undesirable pressure from the prosthetic valve acting outwards towards the aortic valve (which lies adjacent to the mitral valve when viewed in cross section).

The prosthetic heart valve may be self-expanding such that it is biased towards the expanded configuration. The framework can be returned to its collapsed configuration via application of a pulling force on one or more portions of the framework.

The prosthetic heart valve may have any one of or, to the extent that they are compatible, any combination of the following optional features.

In the expanded configuration, the support framework of the prosthetic heart valve may include a saddle-shaped frame structure. The saddle-shaped frame portion would be a three dimensional ring (a hyperbolic paraboloid) and may be made up of one or more pieces of wire. When the three dimensional saddle-shaped frame structure is viewed along the axis of flow of the valve (i.e. from above or below the leaflets) is will have a D-shape. The fluid pathway defined by the framework and associated materials (such as membranes) therefore has a D-shaped cross section.

The prosthetic heart valve may have no more than two leaflets. In this way, a bi-leaflet valve is provided (i.e. it may have no more than two and no less than two leaflets). Such an arrangement is contrast to the mitral valves known in the art as discussed above, all of which have three leaflets. The presence of no more than two leaflets better approximates the natural flow of blood through the site of the native mitral valve.

Furthermore, mitral valves in the prior art, the design of which have been based upon aortic valves, have cross sections (transverse to the direction of flow through the valve) which are circular in shape.

The support framework may be a wire frame bent into a plurality of loops.

The loops may extend outwards from the D-shaped portion in the extended configuration to clamp the prosthetic valve in place.

The collapsed configuration is radially compressed in that the radius of the prosthesis is smaller when collapsed than when expanded. This contraction in radius results in the length along the flow axis (i.e. the longitudianal axis) being longer when the prosthetic heart valve is in the collapsed configuration as each loop is elongated along the longitudinal axis.

The plurality of loops of the support framework may include two petal-shaped loops which extend from the D-shaped annulus at a first side of the leaflets.

In some embodiments, there are no more than two petal-shaped loops.

When the prosthetic heart valve is located at the mitral annulus and is in its expanded configuration, the petal-shaped loops may be located at the ventricle side of the mitral annulus. The petal-shaped loops may extend outwards radially as well as axially from the mitral annulus.

The plurality of loops of the support framework may include two crown-structures which extend from the D-shaped annulus at the opposite side of the leaflets to the petal-shaped loops.

When the prosthetic heart valve is located at the mitral annulus and is in its expanded configuration, the crown sections may be located at the atrium side of the mitral annulus.

In some embodiments, there are no more than two crown structures. In some embodiments, there are no more than three crown structures and one of the three crown structures may be a tension adjusting mechanism.

In some embodiments, when the prosthetic valve is located at the mitral annulus and is in its expanded configuration, the petal-shaped loops engage a portion of the left ventricle such that the loops form clamps into the left ventricle. The crown-structures may also provide a clamping function so that the prosthetic valve is secured in place at either side of the mitral annulus. The crown-structures may extend outwards radially as well as axially from the mitral annulus.

The native leaflets are kept in tension by the petal-shaped loops, which advantageously impedes their movement thereby reducing the probability that they would occlude the left ventricular outflow tract (i.e. the inflow of the aorta).

The crown structures may be filled in or may be open wire structures.

The prosthetic heart valve may further comprise an additional loop at the apex of one or more of the plurality of loops for reducing tension at the apex during transformation between the expanded and collapsed configurations.

In the collapsed configuration, the petal-shaped loops may collapse into elongate arms whereby the length of one elongate arm is longer than the length of the other arm. This arises where at least one petal-shaped loop is of a first size and at least one petal-shaped loop is of a second size, the second size having a larger area than the first size.

This asymmetry between the different collapsed arms means that the collapsed prosthetic heart valve has a smaller radius as compared to a symmetric arrangement because the ends of the arms are located at different positions along the longitudinal axis of the collapsed valve and so do not directly abut against one another. This is particularly relevant in embodiments where an extra loop is located at the apex of the petal-shaped loop.

The reduced radius means that the collapsed prosthetic heart valve is easier to manoeuvre into place which is particularly important for mitral valve location.

In the collapsed configuration, the crown-structures may collapse into elongate arms, the length of one elongate arm being longer than the length of the other arm.

The prosthetic heart valve may comprise a tension adjusting mechanism at the portion of the support framework having a D-shaped cross section. This tension adjusting mechanism may be a portion of wire which acts as a spring.

The forces exerted on the support framework by the tension adjusting mechanism can act to increase and/or decrease tension. The spring provides flexibility in the size of the expanded framework and therefore a better fit.

The portion of wire may be a loop or a partial loop which is additional to the petal-shaped loops and crown structures. In some embodiments it is an extra crown-shaped structure.

Alternatively, or additionally, the tension adjusting mechanism may take the form of a gap in the support framework. This gap may extend along the entire length of the prosthetic valve (i.e. its length along the direction of flow). If the tension reducing mechanism is simply a gap along the length of the support framework, the support framework takes the form of a cuff rather than an incomplete tube. Where the tension adjusting mechanism includes a crown-structure, the crown structure "completes" the circumference so that all parts of the circumference include at least a portion of wire.

The prosthetic heart valve may comprise a cuff attached to the support framework, the cuff providing a seal around at least a portion of the fluid pathway to minimise paravalvular leakage.

In some embodiments, the cuff is a single piece of biocompatible material which extends around the entire framework of the valve providing a seal around the entire outer circumference of the framework. The cuff may be made from soft biological tissue (e.g. pericardium, particularly animal pericardium, intestine, or skin), woven fabric made from a biocompatible polymer (e.g. Polyethylene terephthalate (PET) or Polytetrafluoroethylene (PTFE)), or compact or porous biopolymers (e.g. Silicone, Polyolefin, polyurethanes (PU, PCU, PEU), Polyvinyl alcohol (PVA), etc.

The cuff may comprise a first cuff portion which extends around half of the circumference of the support framework and a second cuff portion which extends around the other half of the circumference of the support framework.

Each cuff portion may be soft tissue having a spherical lune shape when the prosthetic valve is in the expanded configuration.

In some embodiments, one edge of the spherical lune of the first cuff portion is directly attached to the same piece of framework to which the first leaflet is attached. The edge of the spherical lune of the second cuff portion is directly attached to the same piece of framework to which the second leaflet is attached. In this way, the first cuff portion seals potential gaps between the outer edge of the first leaflet and the native mitral valve. The second cuff portion seals potential gaps between the outer edge of the second leaflet and the native mitral valve.

The prosthetic heart valve may further comprise a skirt attached to the support framework.

The skirt may provide additional sealing capability. The material of the skirt may be a mesh in which case it cannot itself perform a sealing functionality. It can however provide support for the cuff.

The skirt may comprise a first skirt portion which extends around half of the circumference of the support framework and a second skirt portion which extends around the other half of the circumference of the support framework.

Where there are two cuffs and two skirts, each skirt provides support for a respective cuff.

Further optional features of the invention are set out below.

BRIEF DESCRIPTION OF THE DRAWINGS

Embodiments of the invention will now be described by way of example with reference to the accompanying drawings in which:

FIG. 6 shows different views of the support framework of a prosthetic heart valve according to the present invention.

FIG. 10 shows a first view 10a and a second view 10b of a prosthetic heart valve in a collapsed configuration, the prosthetic heart valve including two arms of different lengths;

DETAILED DESCRIPTION AND FURTHER OPTIONAL FEATURES OF THE INVENTION

FIGS. 1 to 5 show an example of a prosthetic heart valve suitable for implantation at the mitral annulus of a heart according to the present invention.

The prosthetic heart valve includes a support framework 10 which reversibly transformable between a collapsed configuration and an expanded configuration. FIGS. 1 to 5 all show the expanded configuration.

The support framework is made from wire (such as Nitinol wire) which has been bent to form various framework components. These components include petal shaped loops, in particular two aortic petal-shaped loops (an anterior aortic petal-shaped loop, PSH1 and a posterior aortic petal-shaped loop PSH2; and two mural petal-shaped loops (a mural anterior petal-shaped loop, PSH3 and a mural posterior petal-shaped loop PSH4).

The framework components also include crown structures, including an anterior crown-structure C1, a medial crown-structure C2, and a posterior crown-structure, C3. In FIGS. 1 to 5, the medial crown-structure C2 provides a tension adjusting mechanism and is smaller in size as compared to either of the anterior or posterior crown-structures.

The framework components further comprise additional loops for reducing tension at the apex of respective petal-shaped loops. Each additional loop is located at the apex of a respective petal-shaped loop. The anterior and posterior aortic petal-shaped loops include additional aortic loops in the form of a respective anterior additional loop LO1, and respective posterior additional loop LO2.

The anterior and posterior mural petal-shaped loops include additional mural loops in the form of a respective anterior additional loop LO3, and respective posterior additional loop LO4.

The prosthetic heart valve further comprises two leaflets connected to the framework; an aortic leaflet LF1 and a mural leaflet LF2. The leaflets are flexible membrane components and may be made of soft tissues such as pericardium, polymers or other flexible materials. Each leaflet has a fixed edge which is directly attached to the support framework and a free edge. The free edges of the two leaflets meet and are held against one another to allow fluid flow in one flow direction (from the left atrium to the left ventricle) but not in the opposite flow direction. As can be seen from FIG. 3, the leaflets extend downwards in the direction of flow, such that they contact over an entire contact plane when in contact, the direction of flow through the valve lying within this contact plane.

Figure 1:
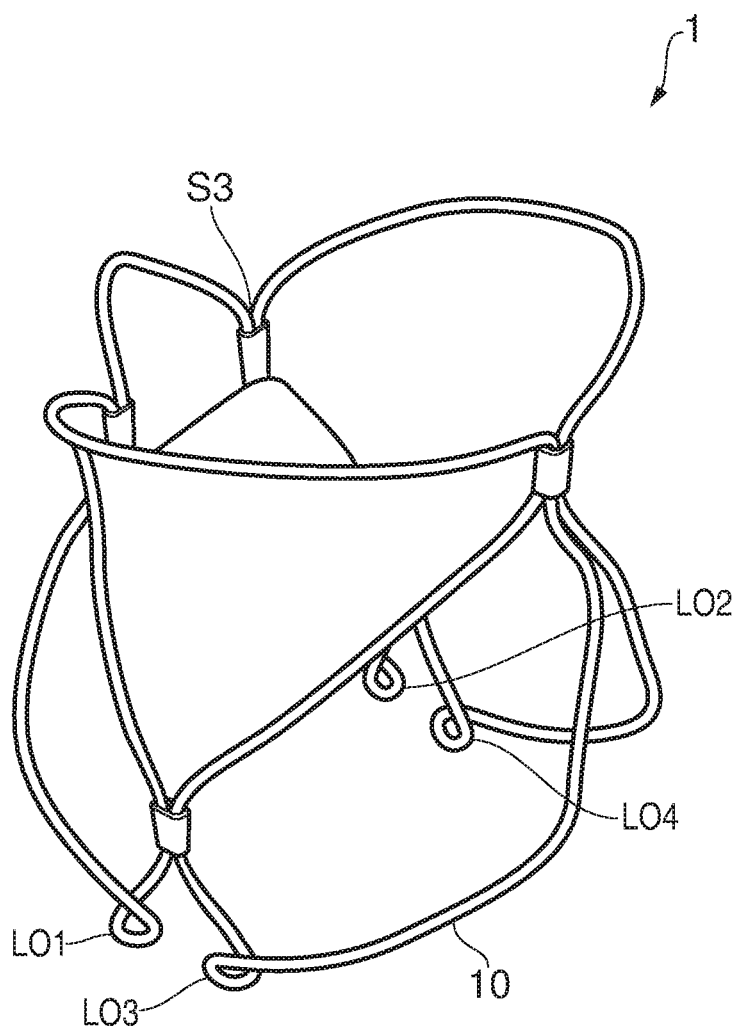
FIG. 1 shows a perspective view of a prosthetic heart valve according to the present invention.
Figure 2:
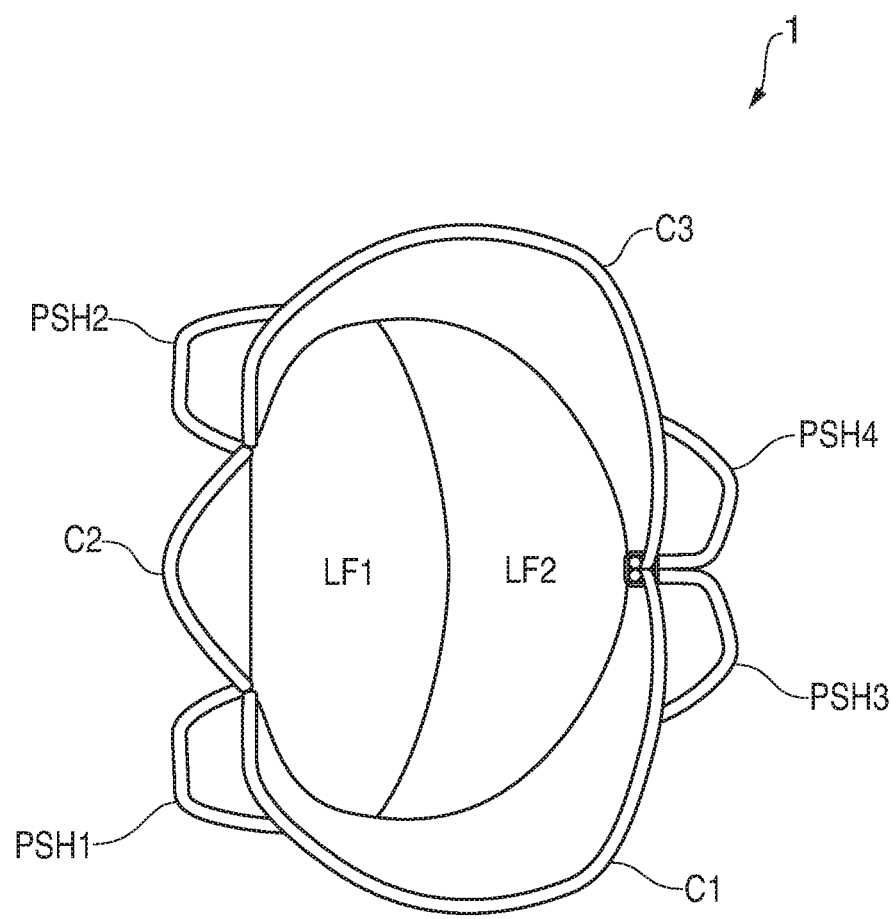
FIG. 2 shows a view of the prosthetic heart valve from the inflow (from the atrial side) according to the present invention.
Figure 3:
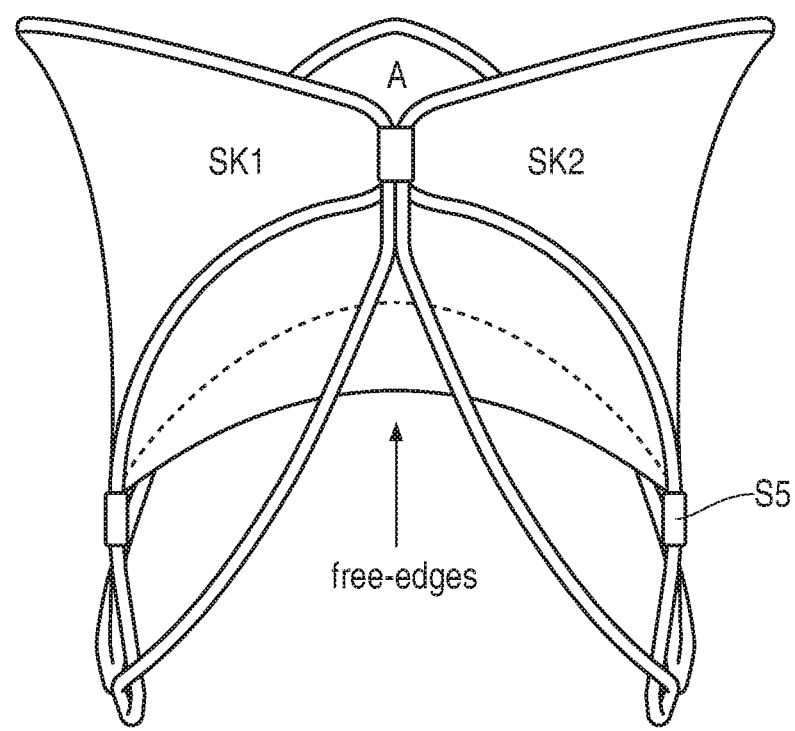
FIG. 3 shows a side view of the prosthetic heart valve according to the present invention.
Figure 4:
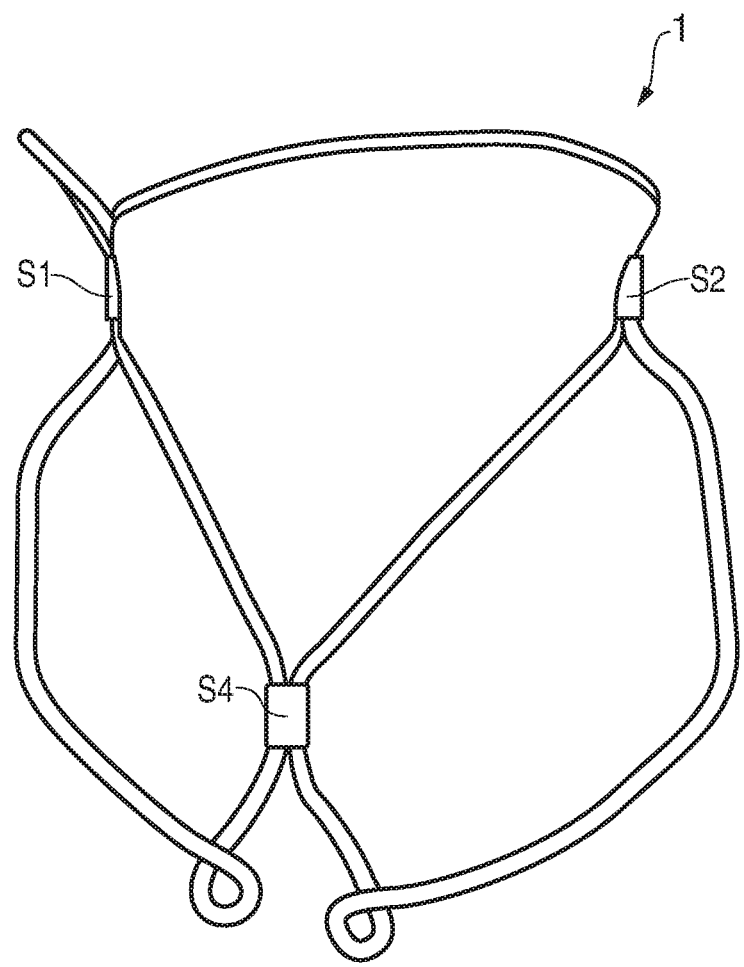
FIG. 4 shows a front view of the prosthetic heart valve according to the present invention.
Figure 5:
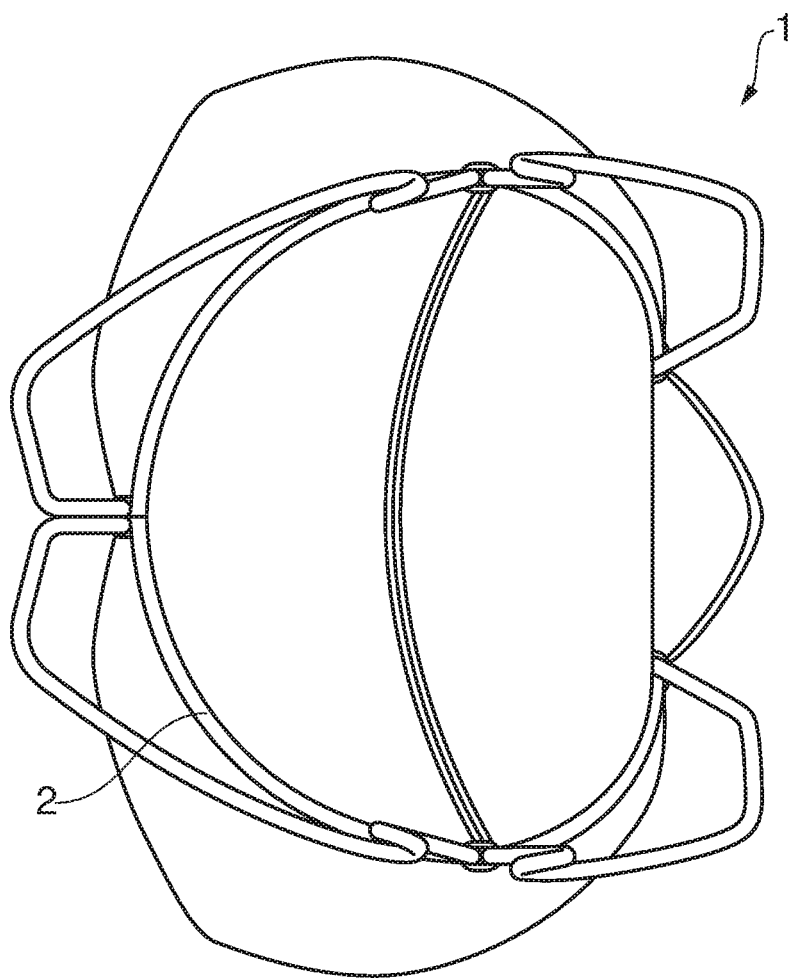
FIG. 5 shows a view of the prosthetic heart valve from the outflow (from the ventricular side) according to the present invention.
Figure 6A:
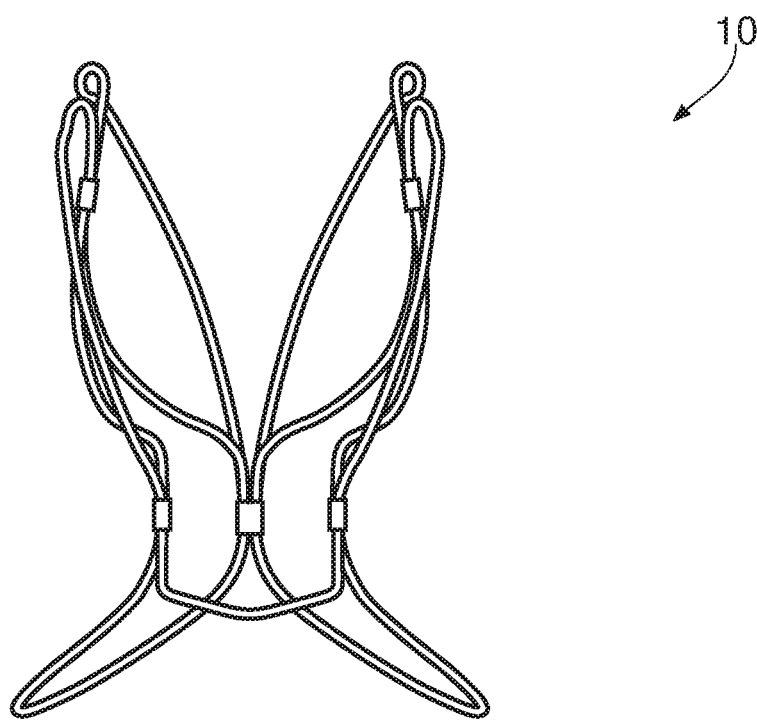
FIG. 6a shows a front view.
Figure 6B:
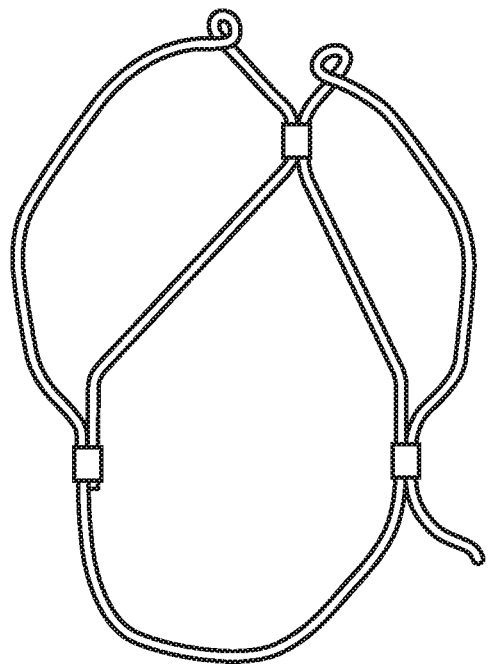
FIG. 6b shows a side view.
Figure 6C:
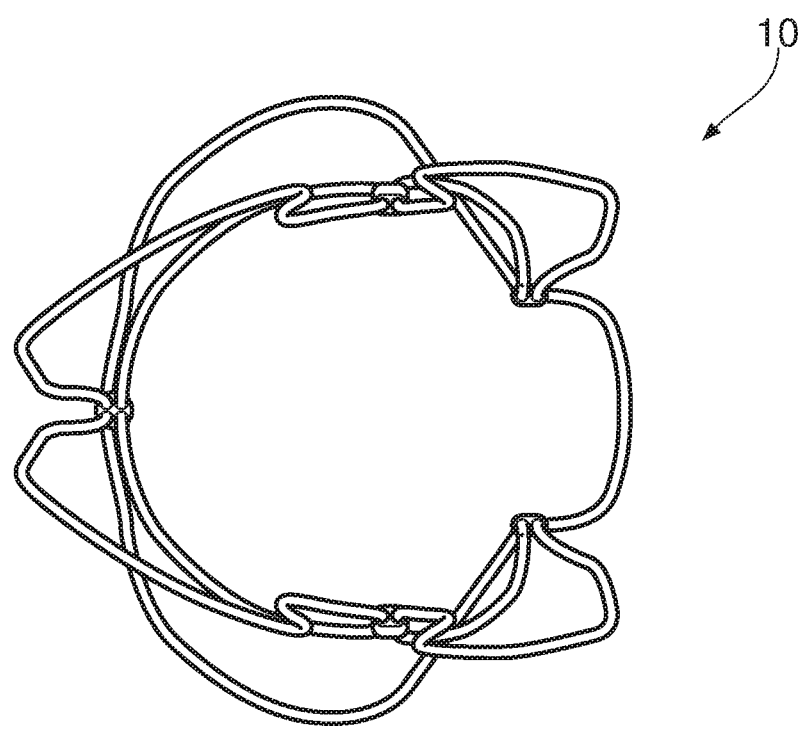
FIG. 6c shows a top view.
Figure 6D:
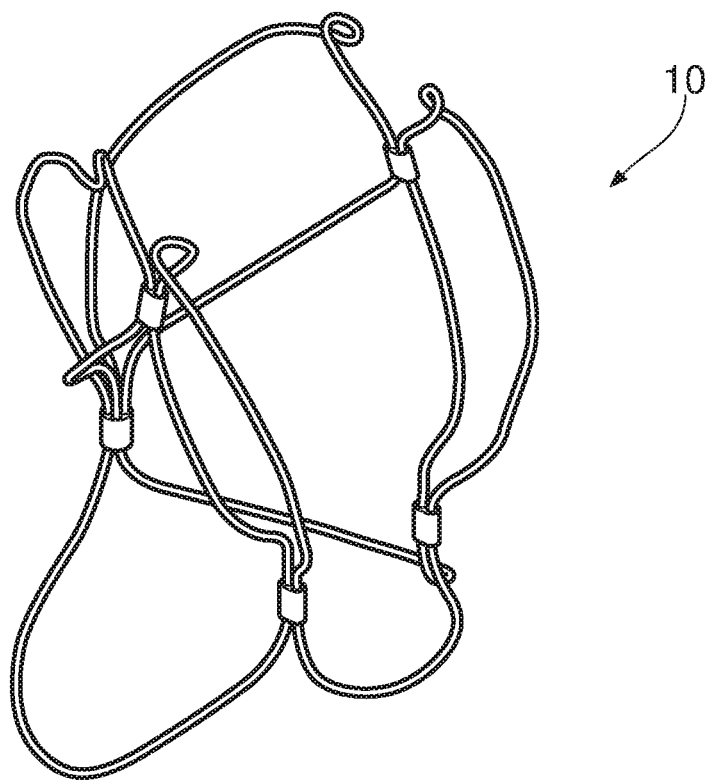
FIG. 6d shows a perspective view.

As can be seen in FIG. 2, the aortic leaflet LF1 has a different shape to the mural leaflet LF2. Thus, the leaflets are asymmetric about the line along which they meet. When viewed along the axis of fluid flow, the aortic leaflet LF1 has a D-shape, whereas the mural leaflet LF2 has a crescent shape.

The prosthetic heart valve includes further flexible membrane components including a skirt, more particularly an anterior skirt component SK1 attached to the anterior crown-structure C1 and a posterior skirt component SK2 attached to the posterior crown-structure C3. The skirts fill in the "holes" defined by the metal frame which marks the boundary of the respective crown-structure.

Further soft flexible membrane components include tissue A which covers the tension adjusting means (the medial crown-structure C2) in the same manner that the skirt components cover the anterior and posterior crown-structures.

Figure 11:
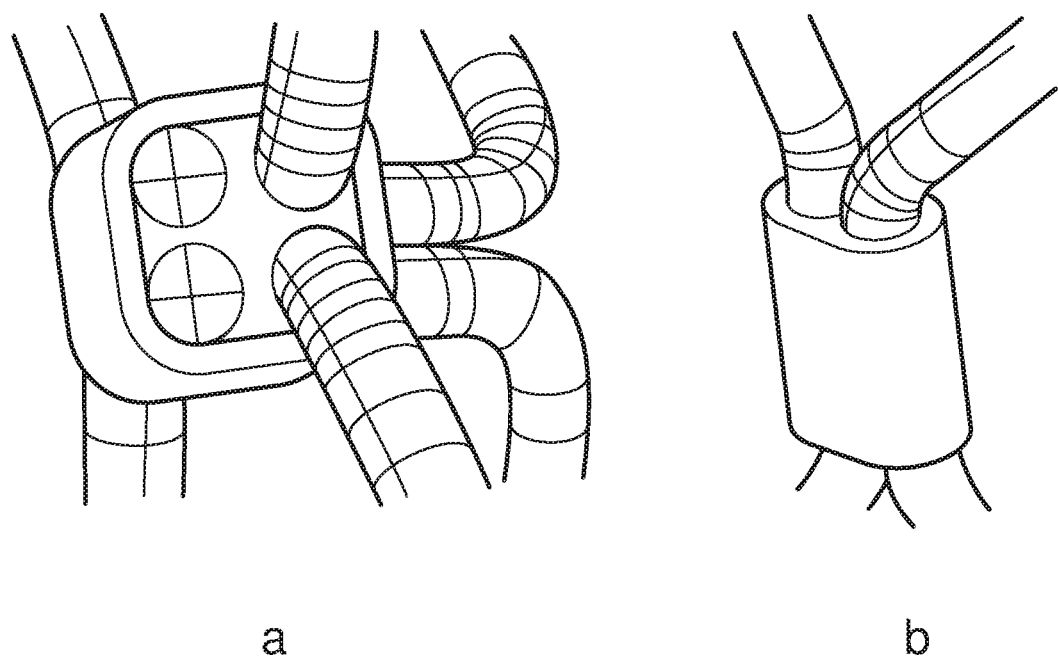
FIG. 11 shows an enlarged view of the support framework of the prosthetic heart valve of the present invention, depicting sleeves on the framework.

The prosthetic heart valve further comprises sleeves S1, S2, S3, S4 which may be made of steel. As shown in more detail in FIGS. 11a and 11b, the sleeves hold together wire portions of the support framework by co-locating the nitinol-wire in five separate locations, preventing rotation. The frame could be made from one nitinol-wire, starting and finishing at the annular-medial-sleeve number S2 (Table 1)(FIG. 2), in which case there would be two sections of the wire in each sleeve, apart from sleeve S2, which would gather four.

The support framework of the prosthetic heart valve would be thermo-mechanically formed, which advantageously provides a relatively cheap manufacturing method as compared to the alternative of laser-cutting of metal tubes.

In the expanded configuration the support framework includes a portion with a D-shaped cross section 2 for engaging the mitral annulus. A three dimensional saddle-shape wire structure forms a pathway that is D-shaped in cross section (i.e. transverse to the axis of fluid flow through the valve).

The one or more leaflets are located at the D-shaped portion as shown in FIG. 2. More particularly, the saddle-shaped wire structure forms an attachment point for the leaflets as shown in FIG. 2, the skirt portions and the cuff portions (the cuff portions are shown only in FIGS. 7d to 7f although it should be understood that the cuffs could be applied to the embodiment of FIGS. 1 to 5). The support framework defines a fluid pathway (along a direction into the page in FIGS. 2 and 5) through the prosthetic heart valve which passes through the saddle-shaped annular portion which has a D-shaped cross-section.

The proposed device is a bi-leaflet, D-shaped, self-expanding heart valve, designed to be implanted inside a native regurgitant mitral valve to restore unidirectional flow of blood from the left atrium to the left ventricle.

The self-expandable nitinol-wire frame 10 is shown in more detail in FIGS. 6a to 6d. The wire frame provides support for the leaflets and anchor the device. The frame is attached to the membrane of the leaflets, along a scalloped edge using thread or alternative joining techniques. The word framework, rather than stent is used to emphases its intricate relationship with the functioning of the leaflets, namely as an axis for their pivoting motion. This is contrary to the metallic stent components of other devices that have the primarily function of exert a radial force on the surrounding anatomy.

The attachment between the wire and the membranes defines where the leaflets and wings (skirts/cuffs) meet. Each leaflet has a "free-edge" which is not attached to the frame, allowing them to move cyclically between open and closed.

The fixed edge of the aortic leaflet LF1 is attached along half of the length of the saddle-shaped wire structure. The fixed edge of the mural leaflet LF2 is attached along the other half of the lengths of the saddle-shaped wire structure. In this way, the entire perimeter of the saddle-shaped wire structure is attached to either one leaflet or another.

The skirts of FIGS. 1 to 5 are enclosed by the frame, acting as a funnel from the atrium to the ventricle during diastole. Whereas the medial crown only partly frames the annex section of the soft tissue, acting as a webbed-spring which can deform and then return to its former shape. This harbours the classical physics of springs in a non-coiled form, enabling the proposed device to adapt to a mobile environment, absorbing movement, whilst providing a consistent radial force securing the device against the mitral annulus, thus creating a seal. In summary, the skirts and annex jointly secure the device and prevent paravalvular leakage.

The mounting of different membranes to the support framework can be further understood with reference to FIGS. 7a to 7e.

Figure 7A:
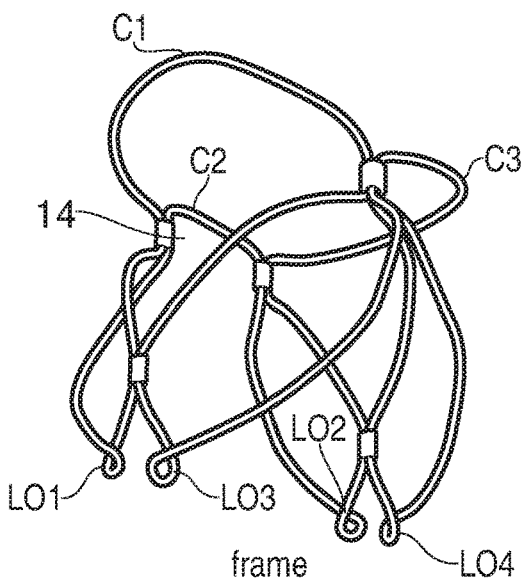
FIG. 7a shows a perspective view of the support framework of an embodiment of the present invention.
Figure 7B:
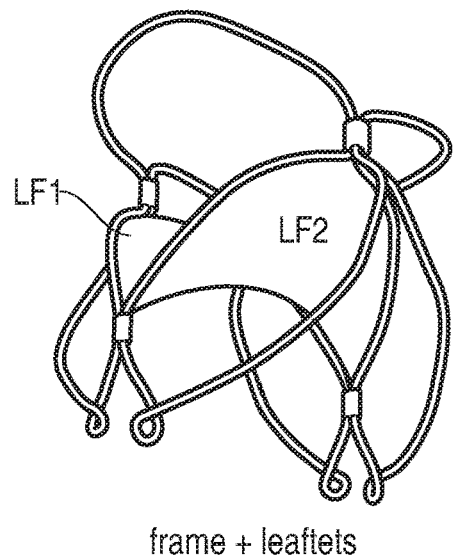
FIG. 7b shows the same support framework, with the leaflets attached.

FIG. 7a shows a perspective view of the support framework of an embodiment of the present invention; FIG. 7b shows the same support framework, with the leaflets attached. Again, it can be seen that the fixed edge of each leaflet occupies a half of the perimeter of the saddle-shaped portion. It should be noted that the two halves of the saddle-shaped portion are not symmetric. One half 14 includes a gap in the perimeter of the saddle-shaped portion which acts as a tension adjusting mechanism. The medial crown C2 bridges the gap, via a sleeved connection with the anterior crown-structure C1, and a sleeved connection with the posterior crown-structure, C3.

Figure 7C:
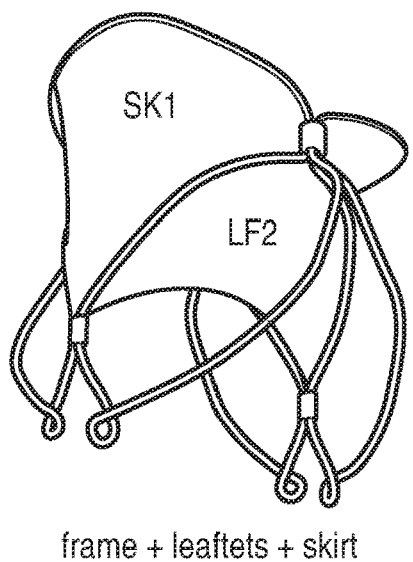
FIG. 7c shows an embodiment of the present invention with leaflets and a skirt attached to the support framework.

FIG. 7c shows an embodiment of the present invention with leaflets and a skirt attached to the support framework. It can be seen that the anterior skirt SK1 extends along and is attached to the half of the saddle-point portion to which the aortic leaflet LF1 is attached. The anterior skirt SK1 also extends along and is attached to the half of the saddle-point portion to which the mural leaflet LF2 is attached. Similarly, the posterior skirt SK2 extends along and is attached to the half of the saddle-point portion to which the aortic leaflet LF1 is attached. The posterior skirt SK2 also extends along and is attached to the half of the saddle-point portion to which the mural leaflet LF2 is attached. Thus a seal is formed between each skirt portion and the adjacent leaflet.

Figure 7D:
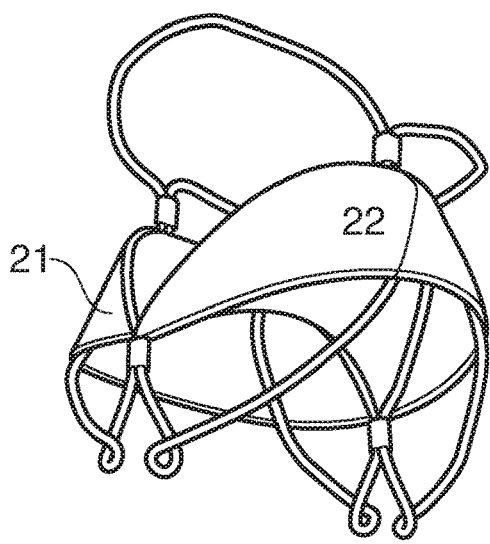
FIG. 7d shows an embodiment with leaflets and a cuff attached to the support framework.

FIG. 7d shows an embodiment which differs from the embodiment of 7b in that it further comprises a cuff attached to the support framework. The cuff is made of a first cuff portion 21 which it attached to the same portion of the saddle-shaped frame as the fixed edge of the aortic leaflet; and a second cuff portion 22 which is attached to the same portion of the saddle-shaped frame as the mural leaflet LF2.

The cuff providing a seal around at least a portion of the fluid pathway to prevent paravalvular leakage. Each cuff portion is a piece of membrane having a spherical lune shape when the prosthetic valve is in the expanded configuration.

Figure 7E:
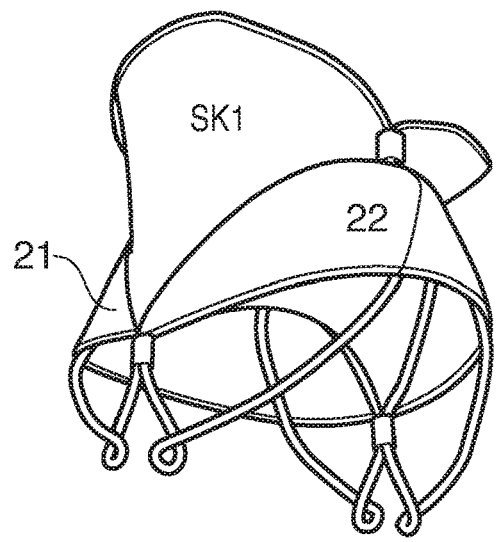
FIG. 7e shows an embodiment of the present invention with leaflets, a cuff and a skirt attached to the support framework.
Figure 7F:
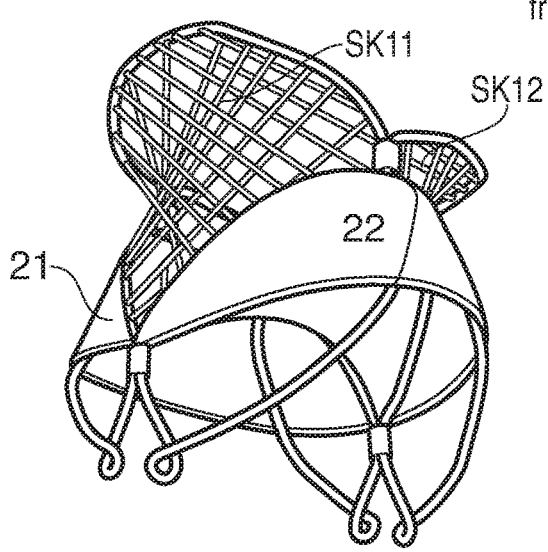
FIG. 7f shows an alternative embodiment with leaflets, a cuff and a skirt all attached to the support framework, the skirt being a mesh.
Figure 7G:
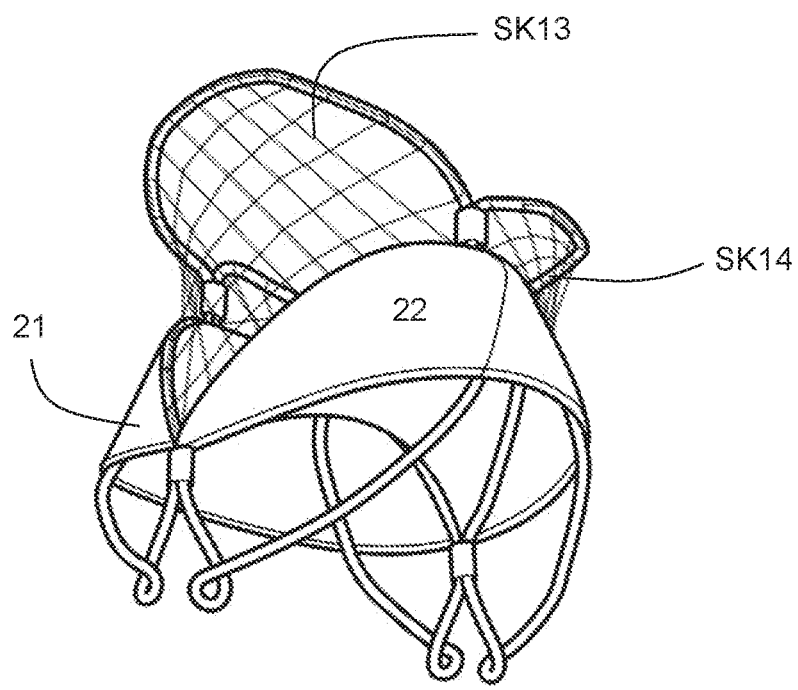
FIG. 7g shows a similar embodiment to that of FIG. 7f, but with a mesh having fibres with a smaller diameter.

FIG. 7e shows an embodiment of the present invention with leaflets, a cuff and a skirt attached to the support framework; and FIG. 7f shows an alternative embodiment with leaflets, a cuff and a skirt all attached to the support framework, the skirt being a mesh. Although the mesh cannot itself perform a sealing functionality it provides support for the cuff. FIG. 7g shows an example of the mesh structure of the skirt in more detail, showing skirts SK13, SK14 made of a fabric mesh with a fine structure. The embodiment of FIG. 7g differs from that of FIG. 7f only in that the diameter of the fibres of the fabric mesh are shown to have a smaller diameter. The mesh can be made from a suitable biocompatible polymer (e.g. Polyethylene terephthalate (PET) or Polytetrafluoroethylene (PTFE)).

Figure 7H:
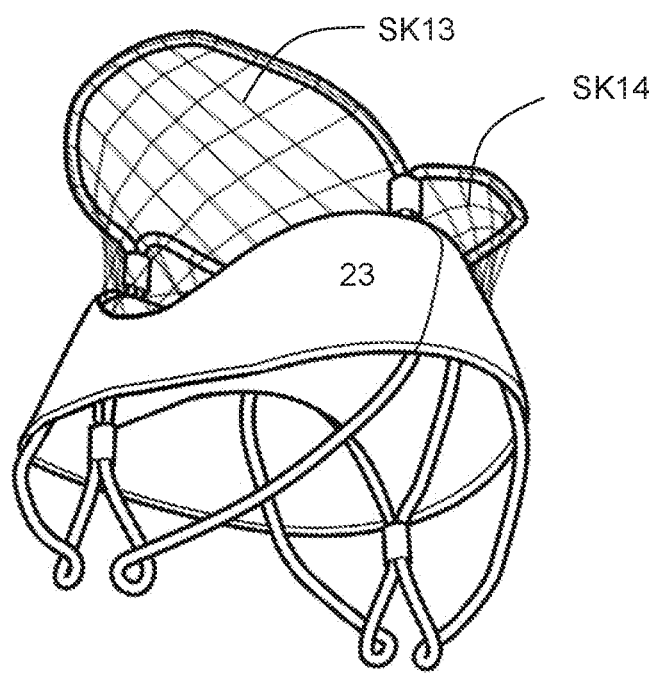
FIG. 7h shows an embodiment with a single cuff which extends the entire way around the support framework.

FIG. 7h shows an embodiment similar to those of FIGS. 7f and 7g, but adapted such that the cuff 23 is a single piece of biocompatible material which extends the entire way around the support framework to provide a seal around the entire circumference of the framework. The cuff can be made from soft biological tissue (e.g. pericardium, particularly animal pericardium, intestine, or skin), woven fabric made from a biocompatible polymer (e.g. Polyethylene terephthalate (PET) or Polytetrafluoroethylene (PTFE)), or compact or porous biopolymers (e.g. Silicone, Polyolefin, polyurethanes (PU, PCU, PEU), Polyvinyl alcohol (PVA), etc. The single cuff has a non-uniform width with two diametrically opposed concave portions and could be applied to any of the embodiments described herein.

Figure 7I:
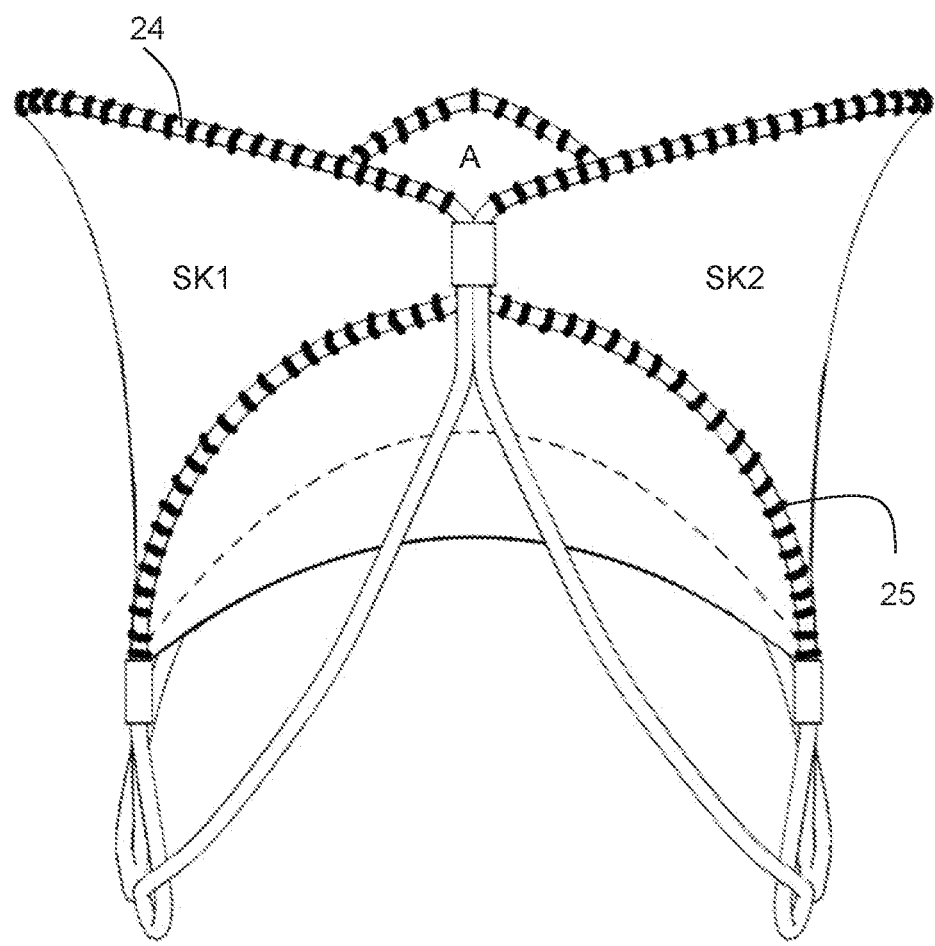
FIG. 7i shows an example of suturing detail.

FIG. 7i shows an example of a mechanism of attachment of the leaflets and skirts to the framework. The biological tissue or biocompatible material used for the leaflets and/or the skirts are sutured directly to the framework, the stitching 24, 25 of the sutures extending along the length of each of the relevant frame portions.

Figure 8:
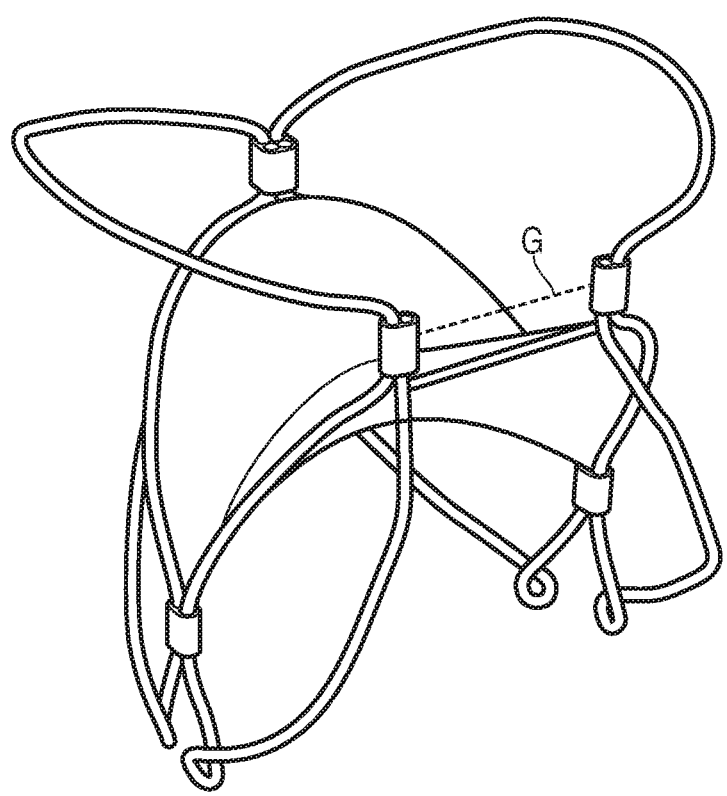
FIG. 8 shows an embodiment of the present invention where a gap in the support framework forms a tension adjusting mechanism.

FIG. 8 shows an embodiment of the present invention where a gap G in the support framework forms a tension adjusting mechanism. This embodiment therefore differs from previous embodiments in that there is no medial crown.

Figure 9:
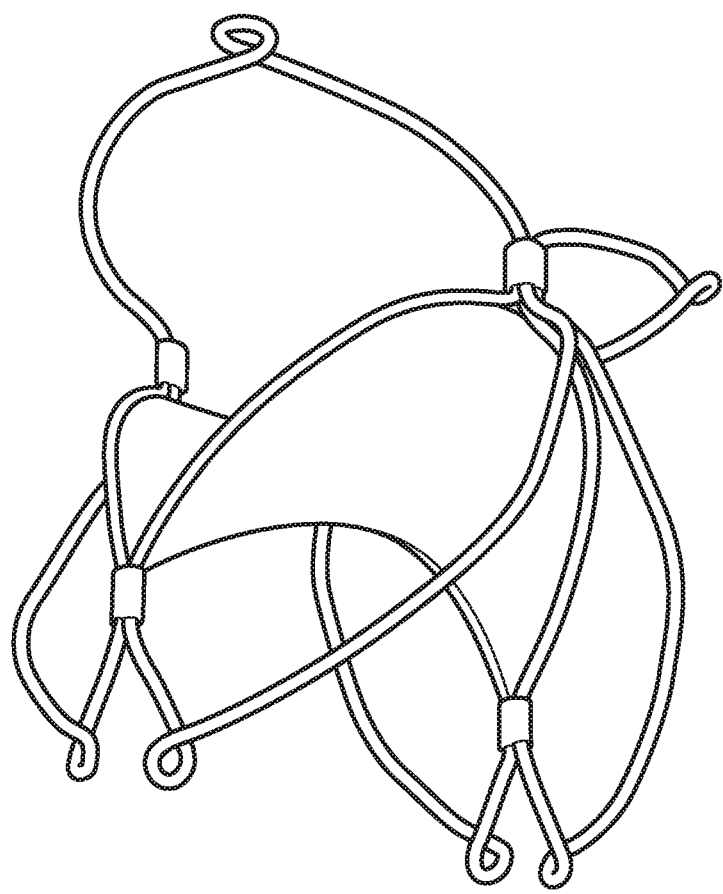
FIG. 9 shows an embodiment of the present invention with additional loops located on the crown-structures and on the petal-shaped loops for improved access from both sides of the native mitral valve.

FIG. 9 shows an embodiment of the present invention with additional loops located on the crown-structures as well as on the petal-shaped loops. This provides for improved access from both sides of the native mitral valve as the loops facilitate collapse of the framework.

Figure 12A:
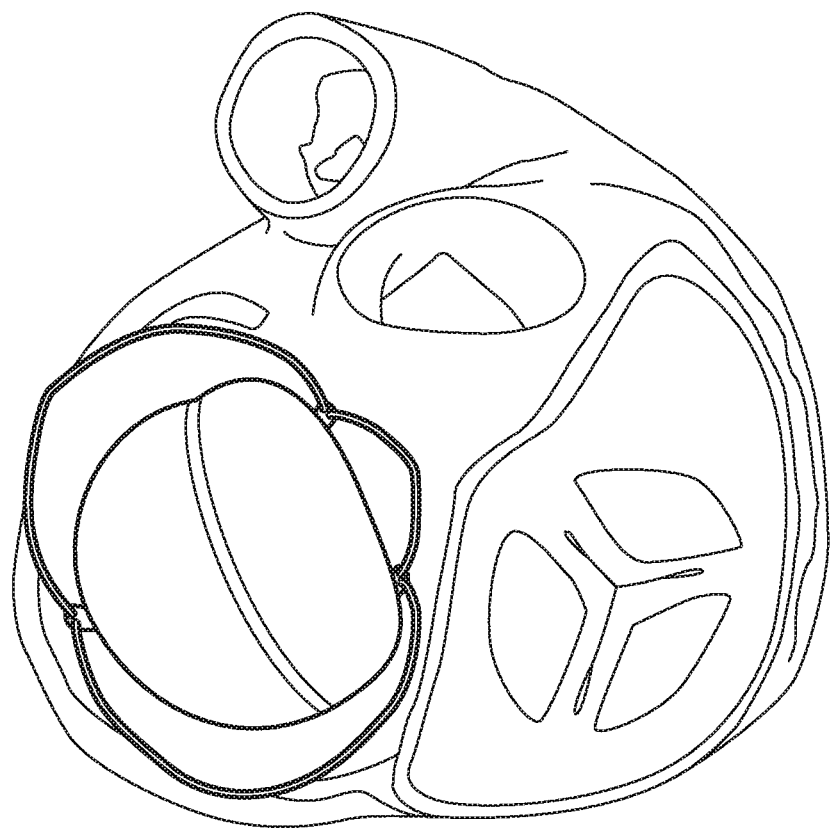
FIGS. 12a and 12b depict alternative views of the prosthetic heart valve of the present invention when in its expanded configuration in location at the mitral annulus of the heart.
Figure 12B:
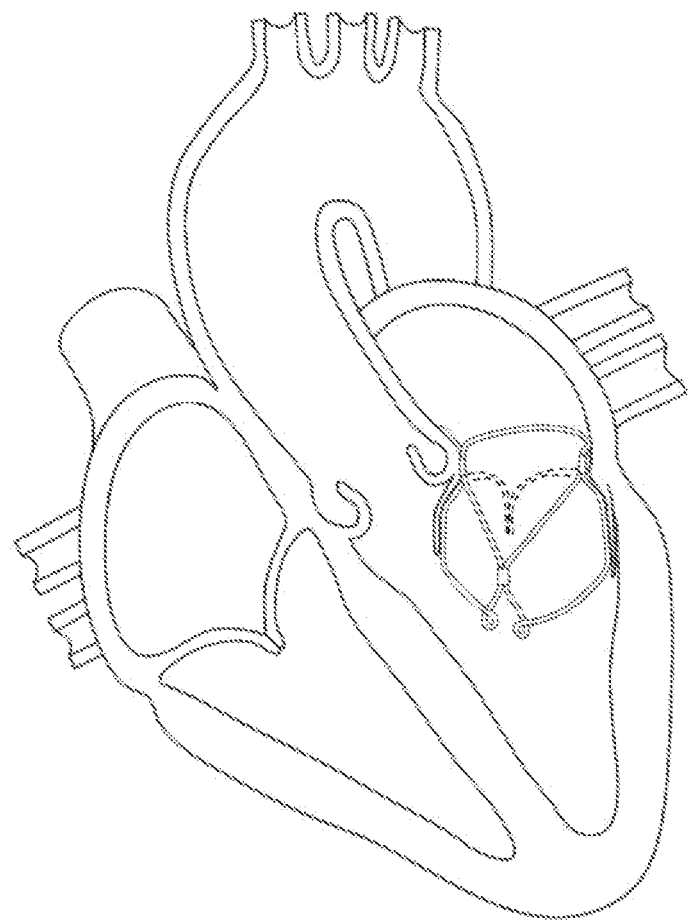

FIG. 10 shows the wire support framework in a collapsed configuration and provides a comparison between a prosthetic heart valve in a collapsed configuration having two arms of a first length 101 and two arms of a second length 102 which is shorter than the first length. Each arm contains an additional loop at its apex. The offset between the looped apex of a first arm 101 and the looped apex of a second arm 102 provides smaller radial dimensions, thereby facilitating delivery of the device to the desired location. The prosthetic heart valve is shown in situ in FIGS. 12a and 12b.

Figure 13:
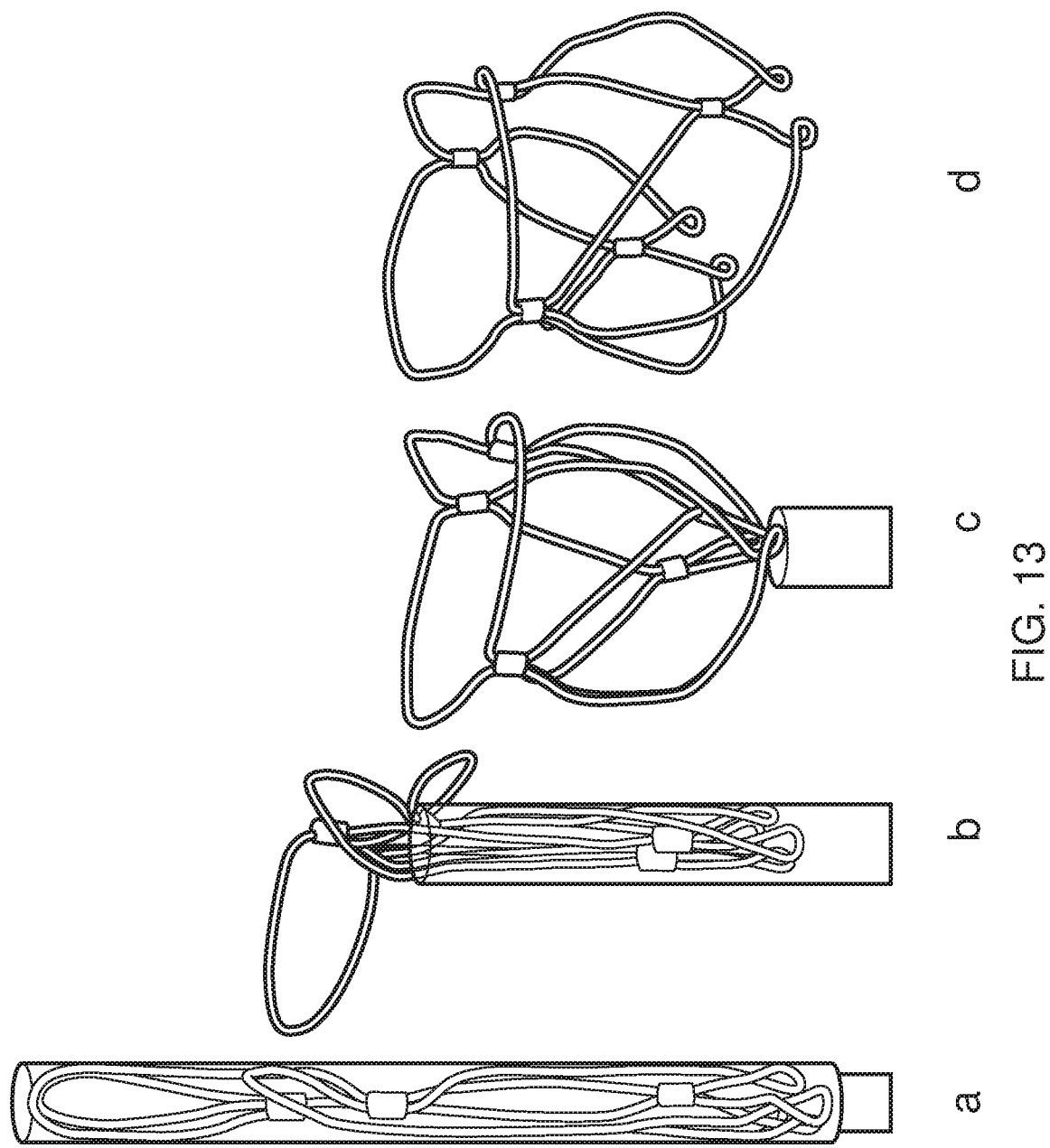
FIG. 13 shows an example of method steps that can be used to transform the prosthetic heart valve from its collapsed configuration to its expanded configuration.
Figure 14A:
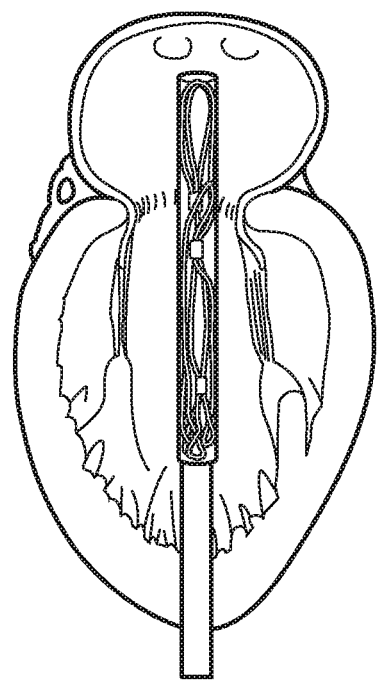
FIGS. 14a to 14d depict stages of a method for deploying a prosthetic heart valve such as that of the present invention at the mitral annulus of a heart.
Figure 14B:
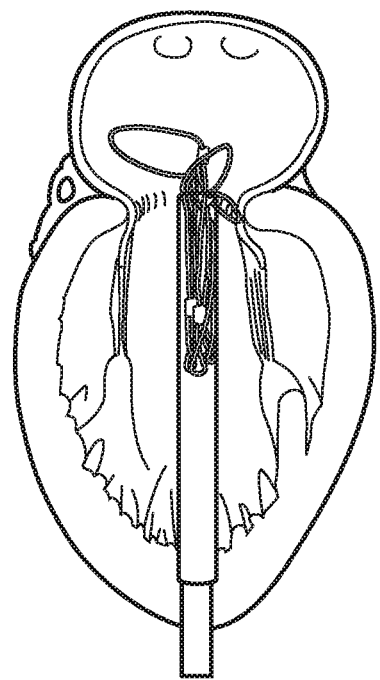
Figure 14C:
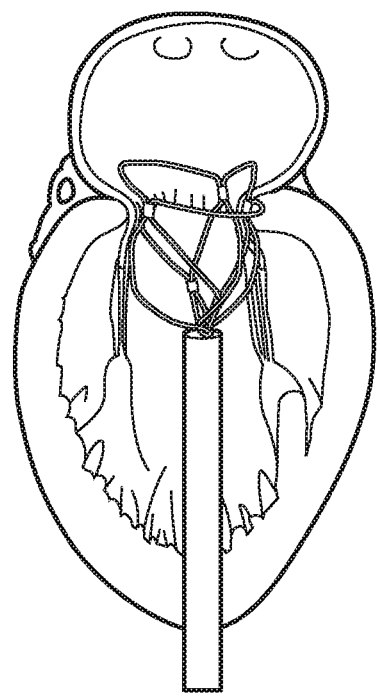
Figure 14D:
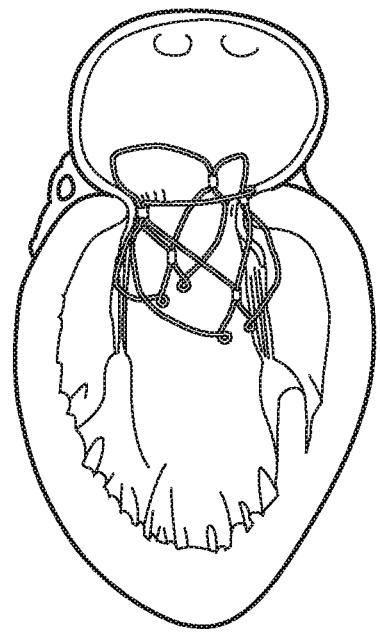

The procedure to implant the proposed device would take place in a catheterisation laboratory. The steps are summarised below with reference to FIGS. 13 and 14. FIG. 13 depicts the process of expansion of the prosthetic valve when outside of the body. FIGS. 14a-d depict the same steps taking place within the heart at the native mitral valve.

As can be seen from both figures, the expansion of the device is a multi-stage process which enables more precise positioning.

Referring first of all to FIG. 13, it can be seen that the multi-stage process includes a first step (a) at which the prosthetic heart valve lies in a collapsed configuration within a catheter. When a force is applied to the valve relative to the catheter (step b), the tips of the crowns C1-C3 will emerge from the end of the catheter. The tips of the crown immediately expand outwards from the tubed confines of the catheter. The catheter is then removed (steps c) to reveal the rest of the prosthetic valve. Once completely free from the catheter (step d) the prosthetic valve will self-expand to take its expanded configuration.

Steps 14a to 14d correspond to steps 13a to 13d respectively but this time carried out inside the body at the site of the native mitral valve. As with all percutaneous heart valves, the proposed device will be loaded into a delivery catheter just before the procedure starts. A set of chords will be threaded through the inside of the catheter. (The delivery is described in more detail in Patent No. WO 2012 052 718 A1), and attached to loops at the other end of the catheter). The chords are pulled to simultaneously crimp and load the device into the catheter (outside of the body, the device may be submerged in water at 4° C. before this step). In the crimped configuration (FIGS. 10a and 10b), the aortic and mural loops are positioned efficiently above one another, and therefore are not on the same horizontal plane when in the open configuration.

It can be seen that in step 14a, the fully collapsed catheter is located at the mitral annulus so that the end of the catheter is located past the mitral annulus, within the left atrium.

Once in this position, pressure is applied to push the valve relative to the catheter (step 14b). The net effect is that the tips of the crowns C1-C3 are exposed. As in FIG. 13b, these tips immediately extend radially outwards (even before the whole of each crown structure has been released from the catheter).

A retrograde procedure is required in FIG. 14 (i.e. a transapical approach), due to the current position of the deployment loops (the additional loops). The three crown sections of the frame would be released in the atrium first forming a stopper rim providing a reference for the correct positioning of the valve as the extended tips of the crowns are used to further position the valve as they can be "hooked" into located at the atrium-side of the mitral annulus. The expanded crown-sections generate one side of the clamping force.

Once the position has been optimised in step 14b, the catheter is pulled back (step 14c) to release the rest of the prosthetic valve, including the petal-shaped loops. This includes the expansion of the petal-shaped-loops inside the ventricle. The loops project outwards radially into the native leaflets, pushing them to the side in a fixed position not interfering with the left ventricular outflow tract and generate the other side of the clamping force, securing the device to the native annulus.

In the event that the device needs to be repositioned, the chords can repeatedly be used to draw the device back into the catheter allowing the device to be repositioned before restarting the deployment. Once the device is confirmed to be in the correct position, the chords are then detached and the additional loops then function as springs, absorbing motions that occur in the light frame structure.

If additional loops are located at the apex of the crown-structures (as shown in FIG. 9) antegrade delivery from the atrial side would be possible.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For example, it is envisaged that instead or as well as sleeves, joining mechanisms such as welding, soldering and/or gluing could be used to connect two or more wire components that make up the framework.

It is also envisaged that an alternative support framework could be obtained starting from a tube instead of a wire, e.g. by laser cutting a metal tube.

All references referred to above are hereby incorporated by reference.

The invention claimed is:

1. A prosthetic heart valve for implantation at a mitral annulus of a heart, the prosthetic heart valve comprising:
   a support framework reversibly transformable between a collapsed configuration and an expanded configuration; and
   one or more leaflets connected to the support framework;
   wherein, in the expanded configuration:
      the support framework defines a fluid pathway through the prosthetic heart valve, the support framework having a portion for engaging the mitral annulus, said portion defining a D-shaped cross section of the fluid pathway;

the one or more leaflets allow fluid to pass through the fluid pathway in a first direction but prevent fluid from flowing in the opposite direction; and a tension adjusting mechanism at the portion with the D-shaped cross section of the support framework to provide flexibility in the size of the support framework when in the expanded configuration;

the support framework further being a wire frame bent into a plurality of loops, wherein the plurality of loops of the support framework includes two petal-shaped loops which extend from the portion with the D-shaped cross section at a first side of the one or more leaflets;

wherein in the collapsed configuration, the petal-shaped loops collapse into elongate arms, a length of one elongate arm being longer than a length of the other arm.

2. The prosthetic heart valve of claim 1, wherein the portion of the fluid pathway comprising the D-shaped cross section includes a saddle-shaped frame structure, the saddle-shaped frame structure having the D-shape when viewed along the axis of flow of the fluid pathway.

3. The prosthetic heart valve of claim 1, having no more than two leaflets.

4. The prosthetic heart valve of claim 1, wherein the plurality of loops of the support framework includes two crown-structures which extend from the portion with the D-shaped cross section at the opposite side of the leaflets to the petal-shaped loops.

5. The prosthetic heart valve of claim 4, wherein in the B collapsed configuration, the crown structures may collapse into elongate crown arms, a length of one elongate crown arm being longer then a length of the other elongate crown arm.

6. The prosthetic heart valve of claim 1, further comprising an additional loop at the apex of one or more of the plurality of loops for reducing tension at the apex during transformation between the expanded and collapsed configurations.

7. The prosthetic heart valve of claim 1, wherein a first one of the petal-shaped loops is a petal-shaped loop of a first size and a second one of the petal-shaped loops is a petal-shaped loop of a second size, the second size having a larger area than the first size.

8. The prosthetic heart valve of claim 7, wherein the tension adjusting mechanism is a gap in the support framework.

9. The prosthetic heart valve of claim 1, wherein the tension adjusting mechanism is a portion of wire which acts as a spring.

10. The prosthetic heart valve of claim 1, comprising a cuff attached to the support framework, the cuff providing a seal around at least a portion of the fluid pathway to prevent paravalvular leakage.

11. The prosthetic heart valve of claim 10, wherein the cuff comprises a first cuff portion which extends around half of the circumference of the support framework and a second cuff portion which extends around the other half of the circumference of the support framework.

12. The prosthetic heart valve of claim 1, comprising a skirt attached to the support framework.

13. The prosthetic heart valve of claim 12, wherein the skirt is a mesh.

14. The prosthetic heart valve of claim 12, wherein the skirt comprises a first skirt portion which extends around half of the circumference of the support framework and a second skirt portion which extends around the other half of the circumference of the support framework.

* * * * *